United States Patent [19]
Wei

[11] Patent Number: 5,824,702
[45] Date of Patent: Oct. 20, 1998

[54] GENISTEIN AS A PREVENTIVE AGAINST ULTRAVIOLET INDUCED SKIN PHOTODAMAGE AND CANCER

[75] Inventor: Huachen Wei, Forest Hills, N.Y.

[73] Assignee: Mount Sinai School of Medicine of the City University of New York, New York, N.Y.

[21] Appl. No.: 657,915

[22] Filed: Jun. 7, 1996

[51] Int. Cl.⁶ .................................................. A61K 31/35
[52] U.S. Cl. ............................................. 514/456; 424/59
[58] Field of Search ................................. 514/456; 424/59

[56] References Cited

U.S. PATENT DOCUMENTS

| | | | |
|---|---|---|---|
| 4,960,908 | 10/1990 | Ito et al. | 549/403 |
| 5,414,015 | 5/1995 | Konoshima et al. | 514/456 |
| 5,506,211 | 4/1996 | Barnes et al. | 514/456 |
| 5,521,516 | 5/1996 | Igarashi et al. | 514/456 |
| 5,545,398 | 8/1996 | Perricone | 514/456 |

OTHER PUBLICATIONS

Sansei, Chem. abst., vol. 103, # 128,809h (1985).
Wei et al, Chem. abst., vol. 119, # 216,833x (1993).
Oka et al, Chem. Abst, vol, 120, # 307,102 v (1994).
Wei et al, Chem. Abst., vol, 122, # 96,450h (1995).
Huachen Wei, Qiuyin Cai and Ronald O. Rahn. Inhibition of UV Light—and Fenton reaction–induced oxidative DNA damage by the soybean isoflavone genistein. Oxford University Press. Carcinogenesis vol. 17 No. 1, pp. 73–77, 1996.
Huachen Wei, Stephen Barnes and Yan Wang. Inhibitory effect of genistein on a tumor promoter–induced c=fos and c–jun expression in mouse skin. Oncology Reports 3: 125–128, 1996.
Hauchen Wei, Ronald Bowen, Qiuyin Cai, Stephen Barnes and Yan Wang. antioxidant and Antipromotional Effects of the Soybean Isoflavone Genistein. Proc Soc Exp Biol Med 208: 124–130, 1995.

*Primary Examiner*—James H. Reamer
*Attorney, Agent, or Firm*—Brumbaugh, Graves, Donohue & Raymond

[57] ABSTRACT

A method of inhibiting the harmful effect of UVR exposure to the human skin comprising topically applying a therapeutically effective amount of genistein to the skin at a time sufficiently close to the time of UVR exposure to inhibit UVR-induced damage to the skin. The genistein appears to act as a chemo preventative agent since it has no appreciable sun blocking effect. The genistein may be mixed with a variety of carriers and skin treatment compositions.

10 Claims, 4 Drawing Sheets

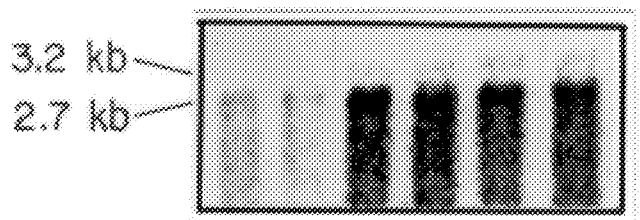
>c-jun  FIG. 4A
—c-fos  FIG. 4B
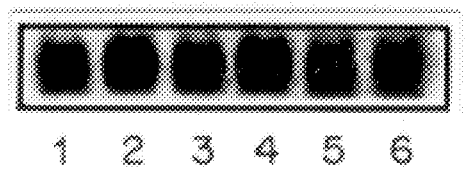
—Cyclo  FIG. 4C
—c-fos  FIG. 6A
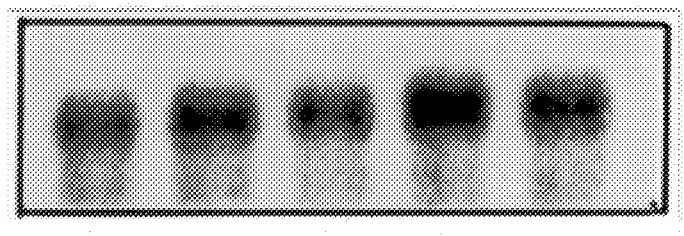
—Cyclo  FIG. 6B 5,824,702

GENISTEIN AS A PREVENTIVE AGAINST ULTRAVIOLET INDUCED SKIN PHOTODAMAGE AND CANCER

BACKGROUND OF THE INVENTION

The present invention relates to the prevention or treatment of skin damage and skin cancer, and in particular to ultraviolet radiation (UVR)-induced skin photodamage and cancer.

It is well documented that long term exposure to ultraviolet light, e.g., sunlight, will damage the skin. Such UVR-induced skin damage includes premature aging, as well as various skin cancers, for example, basal cell carcinoma, squamous carcinoma and malignant melanoma.

While the damaging effects of UVR are known, the recreational and occupational exposure to UVR is a day-to-day fact of life. While some people successfully minimize their exposure, others are either unwilling or unable to do so. For these people, exposure was either accepted as a risk, however unreasonable, or at best was prevented with various heretofore known sun blockers.

Sunscreens or sun blockers physically block the UV rays and thereby lessen the amount of UV light that would otherwise reach the skin. Known products include para aminobenzoic acid (PABA) as well as certain metal oxides. The evaluation of such products is discussed in *Harry's Cosmeticology*, Seventh Ed., pp. 222–263.

The above use of UVR blocking agents is to be distinguished from the use of chemopreventative agents against cancer or skin degenerative processes. Chemopreventative agents function to prevent or alter the various cellular or molecular carcinogenic processes that ultimately lead to tumor growth and the like.

The typical chemopreventative agents, on the other hand, must be administered into the body, such as by oral ingestion, or by injection.

With respect to orally ingested anti-cancer agents, epidemiological studies have shown that consumption of soybean-containing diets have been associated with lower incidence of certain types of human cancers. In particular, the soybean isoflavone "genistein" has been associated with the chemoprevention of cancer. See Wei et al., *Inhibition of tumor promoter-induced hydrogen peroxide production in vitro and in vivo by genestein,* Nutrition and Cancer 20:1–12, 1993; *Antioxidant and Antipromotional Effects of the Soybean Isoflavone Genistein,* Wei et al., Proceedings of Society for Experimental Biology and Medicine, 208: 124–130, 1995.

The purification of genistein from soy products, e.g., soy molasses, is known. See Peterson et al., *Genistein inhibition of the growth of human breast cancer cells; independence from estrogen receptors and the multi-drug resistance gene,* Biochem Biophys Res Commun 179: 661–667, 1991, incorporated herein by reference.

SUMMARY OF THE INVENTION

In accordance with the present invention, it has been discovered that genistein may be used as a topical chemopreventative agent against the adverse effects of UVR on the skin. Genistein may be topically applied, alone or co-administered with other medications, to lessen or prevent UVR-induced skin sunburns, premature aging, and skin cancer.

Genistein is uniquely suitable as a topically applied chemopreventative agent in that it is a natural product having no observed adverse effects or toxicities in humans. The physical and chemical properties of genistein are appropriate for a topical skin agent, i.e., it has high lipid solubility and easily penetrates the skin.

Data suggests that genistein exhibits potent and stable antioxidant activities. It scavenges reactive oxygen species and increases antioxidant enzymes in mouse skin tissue. Thus it may serve to delay skin aging and inhibit skin tumorigenesis.

Since genistein also relieves chemical carcinogen-induced skin inflammation, it may serve as an antiinflammatory agent on chemical skin irritations.

Genistein's ability to inhibit chemical carcinogen-induced protooncogene expression and tumorigenesis permits its use as a chemopreventive agent against chemical-induced carcinogenesis of skin. Genestein's ability to quench UVR-induced oxidative DNA damage in vitro and in cell culture makes it a useful. topical agent for inhibiting the initiation of skin photocarcinogenesis. Moreover, genistein has been shown to suppress UVR-induced protooncogene expression (i.e., in mouse skin) and phosphorylation of the epidermal growth factor receptor in human keratinocytes, thus indicating genistein's ability to inhibit the promotion of skin photocarcinogenesis.

While the possible UVR blocking effect of genistein cannot be entirely discounted, it is genistein's chemopreventive properties that are of particular interest. Thus while the use of a conventional sun-blocking product connotes exactly what the name implies—i.e., that the sun actually be blocked from reaching the skin—a chemo-preventative product need only be typically applied in such a manner that the chemopreventative mechanism function in a therapeutically effective manner.

It is therefore contemplated that such compositions be applied even on the assumption that otherwise harmful UVR or chemical agents will have reached the skin. Included would be the topical application before, during or even after exposure to UVR or other harmful agents, so long as the desired chemopreventive effect can take place to a therapeutically effective extent.

Compositions according to the invention can also be combined with compositions that have other UVR-blocking or antiaging properties. They can also be combined with carriers that will facilitate penetration into the skin, such as DMSO, ethanol:propylene glycol, etc. Finally, the compositions can be combined with compositions that have other cosmetic or medicinal properties, such as skin creams, make-up preparations, tanning lotions or the like.

As noted above, various properties, effects and mechanisms of genistein have been disclosed by the present inventor, although not necessarily as part of the prior art. The above-referenced publications, as well as the prior art and non-prior art publications cited therein, are incorporated herein by reference for purposes of providing background. While some of the properties or mechanisms discussed therein may provide some explanation of the beneficial effects obtained according to the presently disclosed topical uses of genistein, other mechanisms or combinations of mechanisms may be involved.

BRIEF DESCRIPTION OF THE DRAWINGS

The description of the preferred embodiments is further explained below with reference to the figures, wherein:

FIGS. 4 and 6 are photographs of the gel electrophoreses as described in Example 5.

DETAILED DESCRIPTION OF THE PREFERRED EMBODIMENT

Various topical uses of genistein are contemplated by the present invention. These include the prevention or treatment of the affects of UVR on the skin, e.g. premature aging and cancer. Also contemplated is the topical application of genistein as an antiinflammatory agent for chemical skin irritation. These uses are discussed in conjunction with the following examples.

EXAMPLE 1

An experiment was performed to measure the effect of genistein on UV-induced skin erythema.

Figure 1:
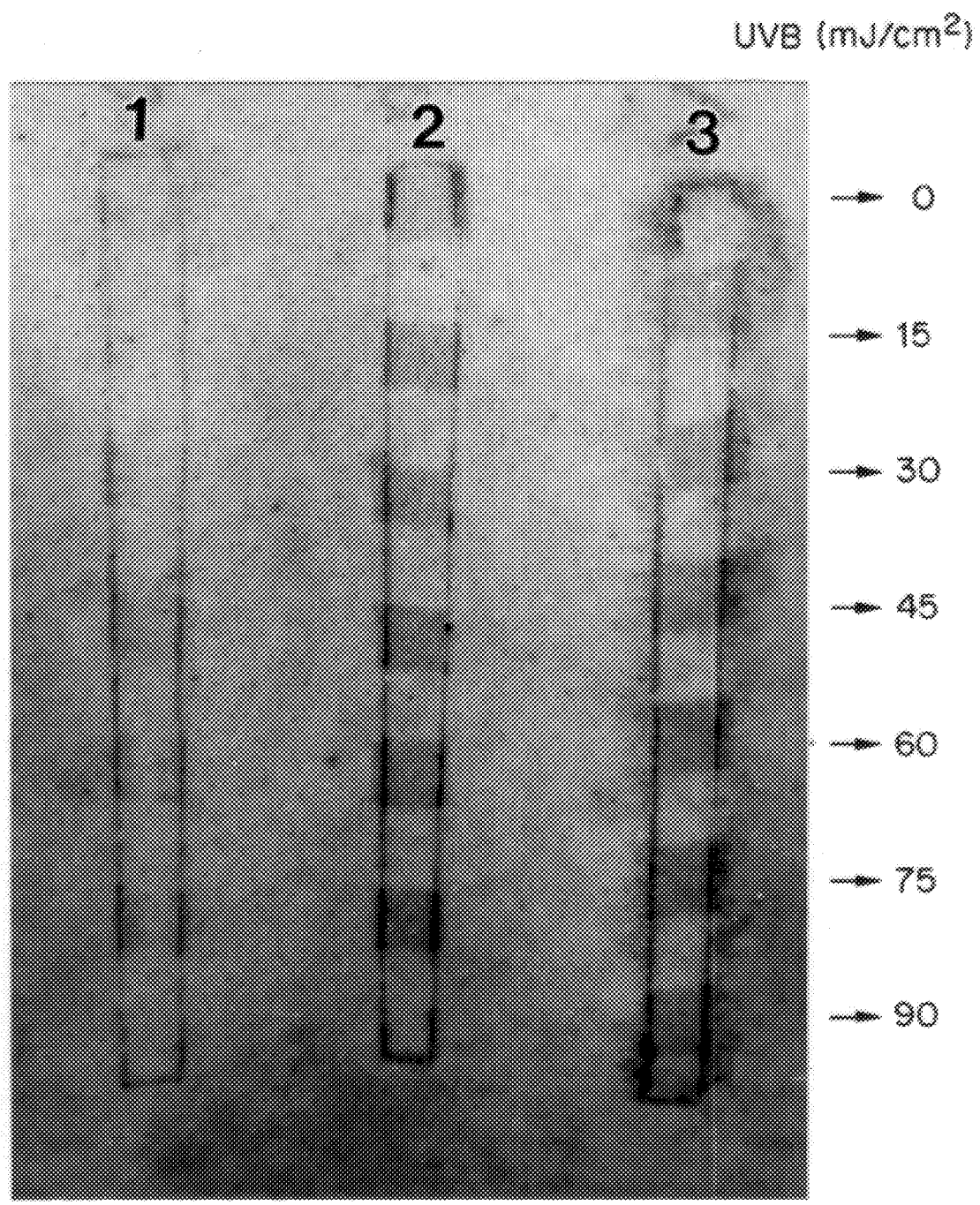
FIG. 1 is a photograph of a patient's back after UVB exposure as described in Example 1.

A human subject was subjected to UVB doses ranging from 0 to 90 mJ/cm$^2$ in three separate "lanes." These Lanes are depicted in FIG. 1.

In Lane 1, the patent was first topically treated with a 5 $\mu$mol solution of genistein per cm$^2$ of skin. The genistein was applied in a 5:95 DMSO:acetone carrier.

In Lane 2, no pre-treatment was given.

In Lane 3, the patient was topically treated with only the DMSO:acetone carrier.

As can be seen from FIG. 1, Lane 1 shows virtually complete protection against skin erythema with the genistein. Both of Lanes 2 and 3 (i.e., no treatment; carrier only) showed UVB dose-dependent induction of skin erythema.

While the mechanism by which genistein inhibited erythema is unknown, the mechanism appears to be independent of the "sunscreen" effect. This was confirmed by dissolving up to 100 $\mu$M genistein in water. No blocking effect of UVB was observed in the genistein solution as compared to the water alone. Methods for testing the sunscreen effect of various compositions are discussed in *Harry's Cosmeticology*, Id.

EXAMPLE 2

An experiment was conducted to determine the effect of genistein dosage on skin erythema inhibition.

The subject was uniformly exposed to a UVB dose of 45 mJ/cm$^2$. The genistein dosage was varied from a high of 5 $\mu$mol to a low of 0.0 $\mu$mol per cm$^2$ of human skin (i.e., 0.0 $\mu$mol; 0.05 $\mu$mol; 0.1 $\mu$mol; 0.5 $\mu$mol 1.0 $\mu$mol; 5.0 $\mu$mol). A striking inhibition of erythema was observed at the 0.1 $\mu$mol level and above. As with Example 1, this inhibiting effect appears to be independent of the sunscreen effect as confirmed by the apparent lack of UV blocking even at a 100 $\mu$mol genistein in water.

EXAMPLE 3

Ultraviolet B (UVB)-induced mRNA, expression of protooncogenes c-fos and c-jun mRNA in the shaven skin of Sencar mice was characterized using the Northern hybridization. When mice were irradiated with the defined doses of UVB (5 and 15 kJ/m$^3$), both c-fos and c-jun expression were induced in a time-dependent fashion. The level of c-fos and c-jun MRNA increased immediately and reached a maximum 1 h after UV irradiation. Expression of c-fos and c-jun appeared to be independent of UV dose.

Figure 2:
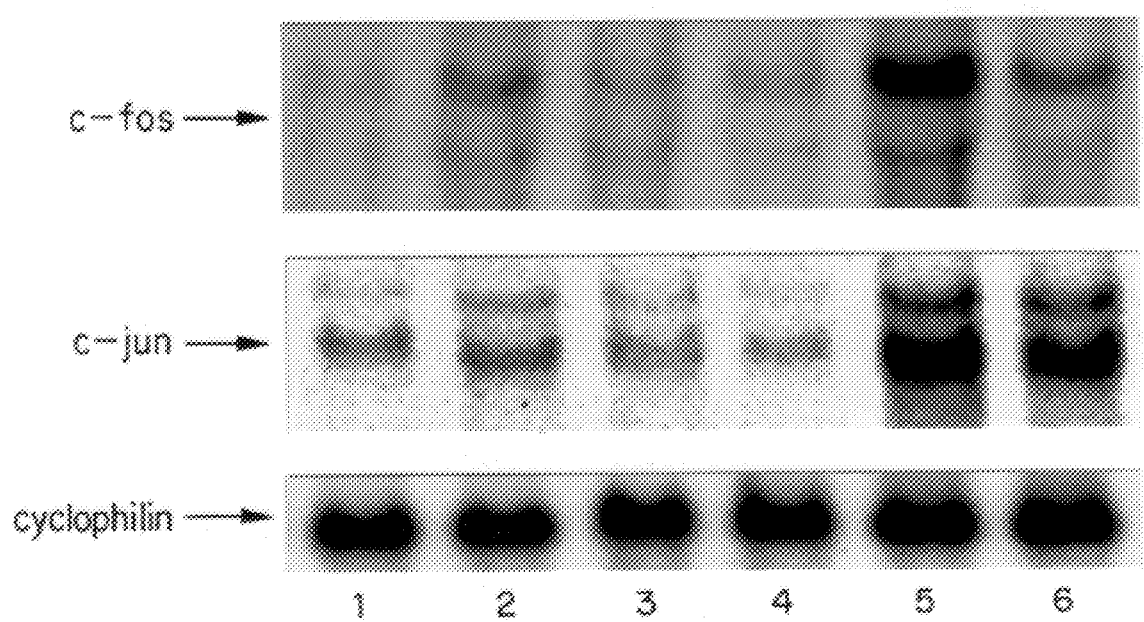
FIG. 2 is a photograph of the gel electrophoresis as described in Example 3.

Topical application of genistein (20 $\mu$mol) 1 h prior to UV radiation substantially inhibited UVB-induced c-fos and c-jun expression induced by a low dose of UVB (5 kJ/m$^2$). At a higher dose of UVB radiation (15 kJ/m$^2$), genistein still substantially blocked UVB-induced c-fos expression, but had little effect on c-jun expression. The inhibition of UVB-induced protooncogene expression in vivo by genistein may be related to the signal transduction pathways because genistein was shown to downregulate UVB-induced tyrosine phosphorylation of epidermal growth factor receptor in cell culture, and mitogen protein kineses in mouse skin. The inhibitory effect of genistein on UV-induced protooncogene expression suggests its potential antipromotional role in photocarcinogenesis. The results of this experiment are shown in FIG. 2. Lane 1 depicts no UV; Lane 2 depicts UV at a dosage level of 5 kJ/m$^2$ (no treatment); Lane 3 depicts 20 $\mu$mol genistein applied one hour prior to 5 kJ/m$^2$ UV exposure; Lane 4 no UV; Lane 5 depicts 15 kJ/m$^2$ (no treatment); Lane 6 depicts 20 $\mu$mol genistein applied one hour prior to exposure at a UV dosage of 15 kJ/m$^2$.

The results of this study were presented at the '96 Society of Investigative Dermatology in Washington, D.C., May 1–5, 1996. An abstract was published in Journal of Investigative Dermatology, 106(4): 856, 1996.

EXAMPLE 4

A procedure similar to that of Example 3 was followed except that the genistein (20 $\mu$mol) was applied immediately after exposure to UVR (15 kJ/m$^2$).

Figure 3:
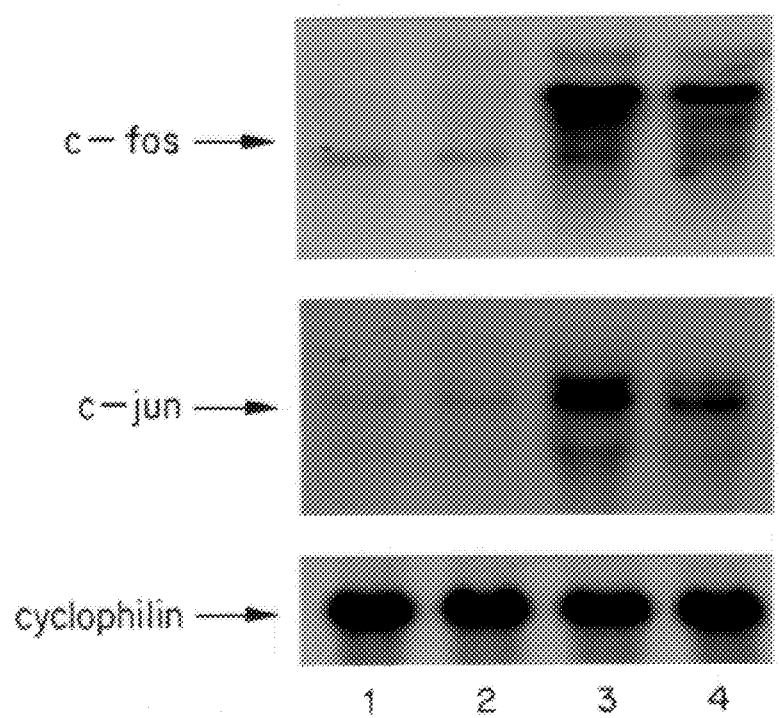
FIG. 3 is a photograph of the gel electrophoresis as described in Example 4.

As shown in FIG. 3, Lane 1: no UV+acetone; Lane 2: no UV+acetone; Lane 3: UV+acetone; Lane 4: UV+genistein. Thus even post-exposure treatment was shown to inhibit c-fos and c-jun expression.

EXAMPLE 5

This experiment was reported in *Inhibitory effect of genistein on a tumor promotor-induced c-fos and c-jun expression in mouse skin*, Wei et al., Oncology Reports 3:125–128, 1996.

FIG. 4 shows that topical application of a promoting dose (8.5 nmol) of TPA significantly induces expression of c-fos and c-jun mRNA in mouse skin (lane 3) compared to the acetone-treated control (lane 1). As reported by Zwiller et al., *Inhibition of PDGF-induced c-jun and c-fos expression by a tyrosine protein kinase inhibitor*, Oncogene 6:219–221, 1991, there are two c-jun mRNA fragments (2.7 and 3.2 kb, respectively), which is due to the presence of two polyadenylation signals. Densitometric quantitation indicates that TPA significantly increases expression of these protooncogenes by 1.7-(c-jun 3.2 kb), 3.2-(2.7 kb c-jun), and 7.0-fold (c-fos), respectively, as compared to the acetone-treated control. Treatment of mouse with genistein alone slightly decreases the basal levels of c-fos and c-jun mRNA (lane 2; 10 $\mu$mol genistein/acetone). However, pretreatment of mouse skin with genistein suppresses TPA-induced induced expression of both c-fos and c-jun (lane 4: 1 $\mu$mol genistein/ TPA; lane 5: 5 $\mu$mol genistein/TPA; and lane 6: 10 $\mu$mol genistein/TPA). Suppression of c-fos expression by genistein is more pronounced than that of c-jun, and at a dose of 10 $\mu$mol genistein, TPA-induced c-fos expression is almost completely inhibited. Hybridization with a cyclophilin probe indicates that mRNA for the tested samples are equally loaded.

Figure 5:
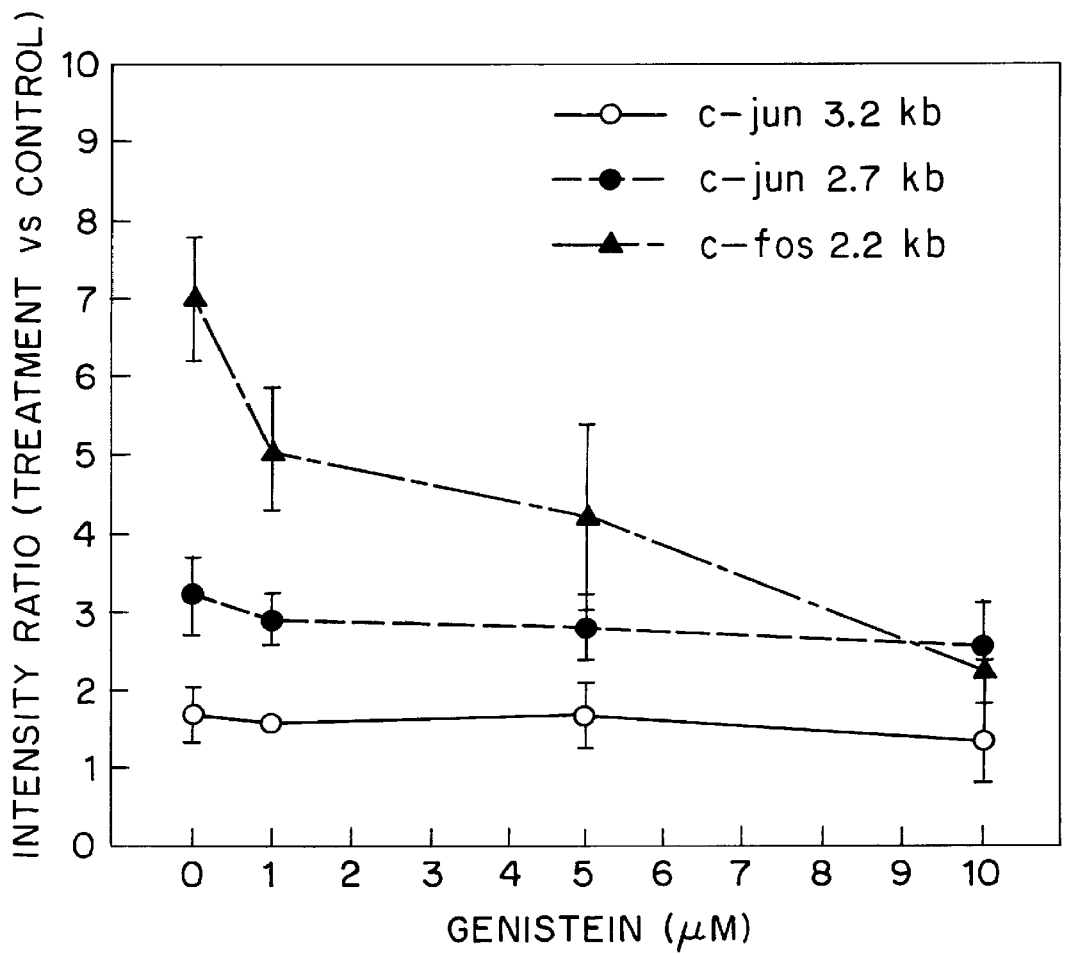
FIG. 5 is a graph showing the quantitation of transcript levels, also as described in Example 5.

FIG. 5 shows the quantitation of transcript levels of c-jun and c-fos from three independent experiments. All results were normalized by their corresponding cyclophilin intensity, and then versus the acetone treated control. The final results were expressed as the intensity ratio (treated groups vs. controls). The background intensity of acetone-treated control was 3.2+4.9 (c-fos), 5.0±1.8 (3.2 kb c-jun) and 9.1±3.9 (2.7 kb c-jun). Expression of both 3.2 kb and 2.7 c-jun mRNA message is only weakly inhibited by about 20% at a high dose (10 $\mu$mol) of genistein. In contrast, genistein strongly inhibits the TPA-induced expression of c-fos in a dose-dependent manner with an apparent $IC_{50}$ of 6.5 $\mu$mol genistein.

FIG. 6 shows the effect of 10 $\mu$mol genistein on TPA-induced c-fos expression at different dosing times. Genistein was topically applied to mouse skin 30 min. before, simultaneously or 30 min. after 5 $\mu$g TPA treatment. Mice were sacrificed 2 h after TPA treatment and skin mRNA was purified. Protooncogene expression was analyzed by the Northern hybridization. A, c-fos and B, cyclophilin. Samples: Lane 1, acetone/acetone; lane 2, acetone/TPA; lane 3, 10 $\mu$mol genistein applied 30 min before TPA; lane 4, 10 $\mu$mol genistein applied simultaneously with TPA; and lane 5, 10 $\mu$mol genistein applied 30 min after TPA. The results show that TPA significantly induces c-fos expression (lane 2) compared to acetone-treated control (lane 1). Genistein can significantly inhibit TPA-induced c-fos expression independent of the different dosing schedules (lanes 3–4).

EXAMPLE 6

The various methods and compositions by which genistein may be topically applied are not limited by the present disclosure. The following is a representative list of suitable compositions:

1) 0.1–5 $\mu$mol genistein/cm$^2$ in 5:95 DMSO:acetone.

2) 0.1–5 $\mu$mol genistein/cm$^2$ in 30:70 propylene glycol:ethanol.

3) 0.1–5 $\mu$mol genistein/cm$^2$ in 2:80 Twean 80:water.

4) 0.1–1 $\mu$mol genistein/cm$^2$ in combination with para-aminobenzoic acid (to absorb UVB).

5) 0.1–1 $\mu$mol genistein/cm$^2$ in combination with benzophenone derivatives (oxybenzone, dioxybenzone —to absorb UVB and UVA).

6) 0.1–1 $\mu$mol genistein in combination with titanium dioxide and/or zinc oxide.

7) 0.1–1 $\mu$mol genistein in combination with vitamins with antioxidant properties, such as vitamin A, vitamin C and vitamin E, including such vitamins in cosmetic moisturizing creams or skin care lotion, particularly for post-UV exposure.

8) 0.1–1 $\mu$mol genistein in combination with other natural products, such as squalene form shark liver oil and aloe vera from liliaceae in cosmetic product.

9) 0.1–5 $\mu$mol genistein added to low SPF sunblocker cream, now commercially available.

10) 0.1–5 $\mu$mol genistein with alphahydroxy acids.

11) 0.1–5 $\mu$mol genistein with Retin-A.

12) 0.1–5 $\mu$mol genistein with betacarotene.

I claim:

1. A chemopreventative method of treatment of the human skin in order to inhibit the harmful effect of UVR exposure to the human skin comprising topically applying a therapeutically effective amount of genistein to the skin at a time sufficiently close to the time of UVR exposure to inhibit UVR-induced damage to the skin whereby said harmful effect is inhibited by a chemopreventive mechanism.

2. A method according to claim 1, comprising applying genistein to the skin prior to exposure.

3. A method according to claim 2, comprising applying genistein to the skin within two hours prior to exposure.

4. A method according to claim 1, comprising applying genistein within two hours of exposure.

5. A method according to claim 1, comprising applying genistein in an amount of at least 0.1 $\mu$mol/cm$^2$ of skin.

6. A method according to claim 1, wherein the genistein is mixed with a carrier in a concentration of from 0.1 to 1.0 $\mu$mol/cm$^2$.

7. A method according to claim 1, wherein the genistein is mixed with a composition having cosmetic or medicinal properties in a concentration of from 0.1 to 1.0 $\mu$mol/cm$^2$.

8. A method according to claim 1, wherein the genistein is mixed with at least one of the following: dimethyl sulfoxide; dimethylsulfoxide:acetone; Twean 80; Twean 80:water; para-aminobenzoic acid; benzophenone derivatives; titanium dioxide, zinc oxide; antioxidant vitamins including vitamins A, C and E; cosmetic moisturizing cream, skin care lotions, squalene; aloe vera; sunblock cream; lipid; alphahydroxy acids; Retin-A; betacarotene.

9. A method according to claim 1 of mitigating the cancer-inducing effect of UVR, comprising topically applying an amount of genistein sufficient to inhibit UVR-induced skin photocarcinogenesis.

10. A method according to claim 1 of inhibiting the skin photo aging effect of UVR, comprising topically applying an amount of genistein sufficient to inhibit UVR-induced aging.

* * * * *

UNITED STATES PATENT AND TRADEMARK OFFICE
CERTIFICATE OF CORRECTION

PATENT NO. : 5,824,702
DATED : October 20, 1998
INVENTOR(S) : Huachen Wei

It is certified that error appears in the above-identified patent and that said Letters Patent is hereby corrected as shown below:

Col. 1, line 5, before "BACKGROUND OF THE INVENTION" insert --This invention was made with government support under Grant Nos. RO1CA60994 and RO1CA61764 from the NIH, such that the United States Government may have certain rights herein.--.

Signed and Sealed this

Twenty-ninth Day of February, 2000

Attest:

Q. TODD DICKINSON

Attesting Officer

Commissioner of Patents and Trademarks